United States Patent
Byrd, III et al.

(10) Patent No.: US 7,077,864 B2
(45) Date of Patent: Jul. 18, 2006

(54) VERTEBRAL INTERBODY CAGE WITH TRANSLATABLE LOCKING SCREW

(75) Inventors: John Abbott Byrd, III, Virginia Beach, VA (US); Jens Peter Timm, Huntington Beach, CA (US)

(73) Assignee: Cross Medical Products, Inc., Akron, OH (US)

( * ) Notice: Subject to any disclaimer, the term of this patent is extended or adjusted under 35 U.S.C. 154(b) by 8 days.

(21) Appl. No.: 10/358,785

(22) Filed: Feb. 5, 2003

(65) Prior Publication Data

US 2003/0153975 A1   Aug. 14, 2003

Related U.S. Application Data

(60) Provisional application No. 60/356,373, filed on Feb. 12, 2002.

(51) Int. Cl.
*A61F 2/44* (2006.01)
(52) U.S. Cl. .................................. 623/17.11
(58) Field of Classification Search ............. 623/11.11, 623/16.11, 17.11, 17.16, 18.11, 23.39, 23.41, 623/23.5, 23.53; 606/60, 61, 72, 73
See application file for complete search history.

(56) References Cited

U.S. PATENT DOCUMENTS

| | | | | |
|---|---|---|---|---|
| 2,437,638 A | * | 3/1948 | Evans | 411/311 |
| 4,351,626 A | * | 9/1982 | Holmes | 411/311 |
| 4,915,426 A | * | 4/1990 | Skipper | 285/288.1 |
| 5,364,400 A | * | 11/1994 | Rego et al. | 606/72 |
| 5,498,265 A | * | 3/1996 | Asnis et al. | 606/73 |
| 5,882,160 A | | 3/1999 | Iwata | |
| 6,053,916 A | * | 4/2000 | Moore | 606/61 |
| 6,193,756 B1 | | 2/2001 | Studer et al. | |
| 6,231,610 B1 | | 5/2001 | Geisler | |
| 6,290,711 B1 | * | 9/2001 | Caspari et al. | 606/232 |
| 6,299,613 B1 | | 10/2001 | Ogilvie et al. | |
| 6,342,074 B1 | | 1/2002 | Simpson | |
| 6,481,760 B1 | * | 11/2002 | Noel et al. | 285/334 |
| 6,558,423 B1 | * | 5/2003 | Michelson | 623/17.11 |
| 6,579,290 B1 | * | 6/2003 | Hardcastle et al. | 606/61 |
| 6,629,998 B1 | * | 10/2003 | Lin | 623/17.11 |
| 2001/0005796 A1 | | 6/2001 | Zdeblick et al. | |
| 2002/0025240 A1 | | 2/2002 | Ward et al. | |

(Continued)

FOREIGN PATENT DOCUMENTS

DE    101 57 969    9/2000

(Continued)

*Primary Examiner*—Eduardo C. Robert
*Assistant Examiner*—Anu Ramana
(74) *Attorney, Agent, or Firm*—Hudak, Shunk & Farine Co. LPA

(57) ABSTRACT

A vertebral cage is provided for use in preserving the space between adjacent vertebral during the process of spinal fusion. In particular, this cage has an open modified oval peripheral shape with a continuous fluid anterior wall having angled screw passages accessible through co-planar openings to allow the construct to be stabilized between adjacent vertebral bodies through their endwalls. In addition, the cage has a back to front wedge taper with pull-out resistant ratchet surfaces. Further, in a second aspect of the invention, the screw passages have a unique locking mechanism provided by oversized internal threads in combination with a second locking thread on the head of the associated bone screws that allows for axial translation of the screws within the screw passages. This in turn permits play in the angulation of the screw relative to the anchoring bone in order to optimize the screw placement in the bone.

37 Claims, 3 Drawing Sheets

U.S. PATENT DOCUMENTS

| | | | |
|---|---|---|---|
| 2002/0099376 A1* | 7/2002 | Michelson | 606/61 |
| 2003/0125739 A1* | 7/2003 | Bagga et al. | 606/61 |
| 2003/0130737 A1* | 7/2003 | McGahan et al. | 623/17.11 |
| 2003/0153919 A1* | 8/2003 | Harris | 606/69 |

FOREIGN PATENT DOCUMENTS

| | | |
|---|---|---|
| WO | WO 00/66045 | 11/2000 |
| WO | WO 01/80785 | 11/2001 |
| WO | WO 01/95837 | 12/2001 |

\* cited by examiner

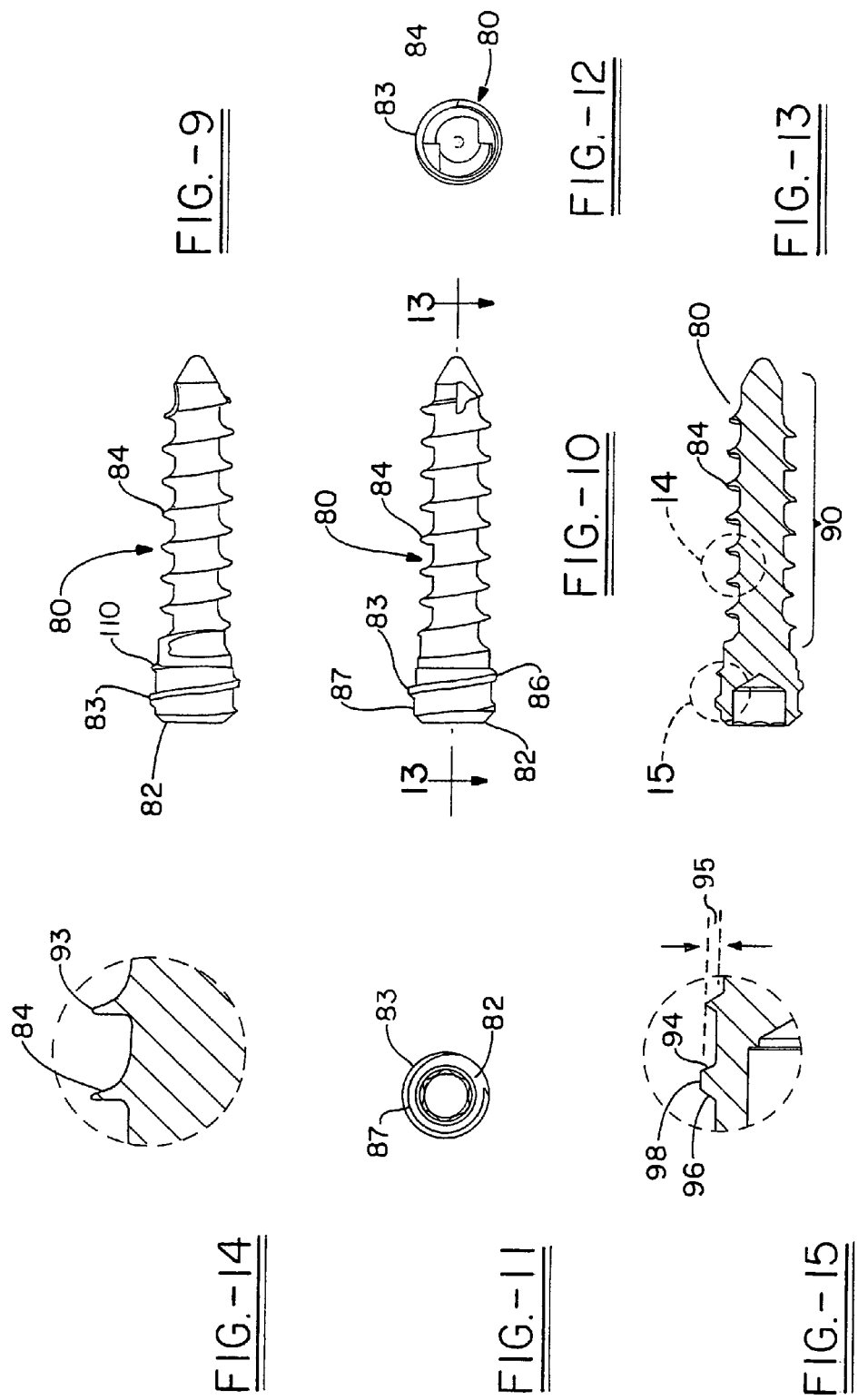

VERTEBRAL INTERBODY CAGE WITH TRANSLATABLE LOCKING SCREW

This patent application is based upon U.S. Provisional Application Ser. No. 60/356,373, filed Feb. 12, 2002.

The invention relates to a vertebral cage for use in preserving the space between adjacent vertebrae during the process of spinal fusion. In particular, this cage has a back to front wedge taper and an open modified oval peripheral shape with an anterior wall having angled screw passages to allow the construct to be stabilized between adjacent vertebral bodies through their end-walls. Further, in a second aspect of the invention, the screw passages have a unique locking mechanism in combination with the associated bone screws that allows for axial translation of the screws within the screw passages. This in turn permits play in the axial and radial position of the screws in the screw passages and in the angulation of the screw relative to the anchoring bone in order to optimize the screw placement in the bone and to minimize threading difficulties such as cross threading.

BACKGROUND OF THE INVENTION

The flexible structure of the spine is provided by a series of interlocking individual members or vertebrae that are naturally shaped and aligned to provide a gentle undulation which causes the spine to have a gentle S-shaped curve. The vertebrae, each have a drum shaped front, (i.e. anterior portion), the vertebral bodies, collectively aligned to form a column and a rear, (i.e. posterior portion), the pedicles, lamina and spinous processes that interlock at the back of the spine. The vertebral bodies have generally oval-shaped top and bottom plates, (i.e. end plates), of hard cortical bone which surround the softer interior cancellous bone. The spaces between the vertebral bodies are maintained by intervertebral discs which are comprised of a tough outer fibrous material which encases a softer gelatinous mass.

In a healthy spine, the cervical and lumbar areas curve forward, i.e., they are lordotic, while the thoracic region curves in reverse of this. The discs act as spacers to maintain the position of the vertebrae and to transmit and absorb loads between the hard bones of the vertebral bodies.

The intervertebral discs include a taper, or wedge shape which help to define the relative position of the vertebral bodies and to cause the curve of the spinal column. However, it is possible for these discs to lose their shape through traumatic damage or long term degeneration. This condition can result in a loss of the normal spinal curvature or of proper alignment of the vertebrae. As a result, the natural transmission of loads in the spine may be seriously impaired with attendant loss of function and back pain.

An accepted treatment for disc degeneration is to remove the degenerative disk and promote fusion of the remaining adjacent vertebrae. Typically, this procedure incorporates the use of an invertebral body spacer in conjunction with bone graft material that promotes the growth of two vertebrae into a solid segment. The spacer is used to maintain the desired spacing and alignment while the bone graft or bone growth promoting material promotes the fusion of the vertebrae for long term stability. During the fusion process it is desirable to inhibit any relative movement of the vertebrae that are involved.

Various structures have been designed to act as interbody spacers or cages. Implantation of these structures may occur from an anterior, posterior, anterolateral or lateral position. The vertebral spacer or cage of the present invention is designed for anterior insertion, but may also be implanted anterolaterally or laterally. This cage forms a tapered circlet which can be envisioned as a closed bracelet shape. It may have a taper in height from front to back to provide a wedge shape from front to back. It has an opening in its center which receives bone graft material. Side fenestrations, or open areas permit radiographic examination of the fusion process. Further, the peripheral outline of the disc defines generally concentric interior and exterior walls. At the front, or anterior surface, the cage has a substantially solid and smooth or fluid wall (the term "fluid" is used herein to mean that this surface is substantially continuous and devoid of sharp transitions or edges). The anterior wall has screw passages therethrough for countersunk screw heads. Further there are a pair of openings in the anterior face that can be used alone, or in combination with a pair of lateral recesses for instrumentation used during implantation. The anterior wall is substantially solid with a "flat" or fluidly continuous surface with coplanar access openings corresponding to a plurality (i.e., two and preferably three) of angled and preferably internally threaded passages. Advantageously three screws can be used wherein one project at one angle up or down and the other two are angled so as to splay in the opposite direction. This provides for a triangular base of fixation that is an advantage over two screws in helping to prevent rotation of the cage about the axis of the spinal column. This stability furthers an object of the invention to provide for relative stability of the adjacent vertebrae to facilitate spinal fusion.

The screw passages permit fixation means, and preferably screws to be inserted through the anterior wall of the cage through the end plates into the cancellous portion of adjacent upper and lower vertebrae to fix the vertebrae and the cage in position.

Further to hold the vertebrae and cage in position, the cage has a high friction surface which is illustrated in particular as a toothed, or ratchet surface to inhibit the cage from being pressed forward out of position. While this is the preferred surface, other contoured high friction surfaces could be used, having a combination of grooves or roughened or machined contours.

The cage is made from suitable strong and bio-compatible material such as titanium, surgical grade stainless, carbon composite, ceramic or the like.

As a separate aspect, the implant of the present invention (notably the substantially solid wall of a vertebral cage) has a unique locking screw assembly.

The issue of implant fixation using a bone screw has deserved and received significant attention by those skilled in the art. These issues are made more complex than more standard problems associated with the use of a screw to join two components by a number of factors. First, the screw and construct are not merely static, but become part of a dynamic system including the surrounding skeletal components as acted on by the soft tissues. Thus, the construct are often subject to large and quickly varied loads, including loads which might be applied during surgery to oppose strong muscular loads and to correct postural alignment. Thus, a skillful surgeon may actually use the stabilization construct to manipulate the components prior to fixing the construct to achieve the desired stabilization. Therefore, the anchoring mechanism is the skeleton which can be subject to significant stress. The best thread purchase can be achieved in the cortical layer of the bone, which is hard but brittle, and might therefore easily fracture. Cancellous bone allows a longer run for thread capture, but is softer, and more spongy in its consistency. In any case, while exact placement issues may be critical, the bone is relatively unforgiving to allow multiple attempts at fixation, particularly if the bone quality is compromised as it might be in cases that require surgical intervention. Second, the construct must be designed so that it is as benign as possible for implantation and afterwards. Components which may irritate or damage surrounding sensitive soft tissue are to be avoided. This is critical for anterior thoracic lumbar implants since this area is adjacent to important blood vessels. Thus, it is desirable to maintain fluid exterior implant shapes with low profiles, while maintaining sufficient material to ensure the structural integrity of the parts. It is critical to avoid shearing, splintering or breaking of the implants. Third, the complexities of the surgical context must be kept in mind. While the components are often relatively small they need to be easily assembled and "unfussy". Thus, elegance in design is imperative. This is especially true since constructs may include numerous repetitive component parts or points of fixation. Thus, a time savings for a single sub-assembly may be multiplied for a number of such sub-assemblies. It is important that the parts go together easily, and can be disassembled if necessary. Problems such as cross-threading and incomplete assembly are to be avoided where possible. Fourth, the site of implantation may be difficult to access deep in the patient's body requiring the surgeon to utilize extended instruments through strong and thick muscular tissue to access the implantation site in an environment that causes limited visibility. Finally, the structure of bone must be kept in mind with respect to the issue of fixation.

In view of the foregoing concerns, one of the issues in the use of screws for implant fixation is inhibiting the screw from backing out of an implant recess. The implant may include the previously mentioned vertebral cage, or may also include any number of other implants including for example, plates, rod systems, holding flanges, and basically any internally threaded (and preferably through bore) implant component. Despite the broad range of applications for the self-locking screw assembly of the present invention, it is of particular advantage with the vertebral cage of the present invention since it allows for locking of the screw in the implant as well as for axial translation of the screw in the passage, and accordingly for play in the angulation of the screw, both movements being relative to the longitudinal axis of the screw and of the screw passage. This is very helpful to allow the screw to be fully screwed into the adjacent vertebral bodies so that the terminal surface or head of the screw will reside substantially flush with or below the smooth anterior surface of the cage defined by the access opening to the screw recesses. Thus, the screw can be tightened into a snug or locked engagement in the cage while drawing the cortical ring of the adjacent vertebral bodies unto the high friction surface of the cage, and the head can reside substantially, or fully within the screw recess to avoid the risk of contact with veins that run along the anterior portion of the spine.

The self-locking assembly comprises a specifically designed screw passage having female threads which are sized beyond the generally acceptable tolerances for the male threads of the fixation screws. Thus, while the pitch is about 0.1 inch, meaning the longitudinal distance needed to achieve one full rotation (360°) of thread spiral, is the same for the male and female locking threads. The profile of the locking thread of the male thread form is significantly smaller than the corresponding profile of the female locking thread form. The width of the thread profile for the male head is approximately two thirds of the corresponding thread profile in the female thread. The depth of thread engagement of the male thread form is approximately 90% of the depth of the corresponding female thread form. The cancellous thread on a first longitudinal screw area has a typical asymmetrical cross-section with a sharp spiral edge, while the locking thread on the second screw area (i.e., the head) has a symmetrical trapezoidal cross sectional shape which is about 60° on the front thrust surface or leading surface and the same on the back measured from the flat transverse plane of the spiral face which is less than 0.04 inch deep.

The thread of the first section (the cancellous section) forms a continuous, but interrupted spiral path with the thread of the second section (the locking section). Essentially, the male thread has a narrower foot print with a smaller major diameter) whereas the female thread has a narrower spiral ramp and a wider groove. This allows the screw to be translated along the longitudinal axis, which will change the relative radial position of the spiral thread at the point of entry in the bone. Also, there is play with respect to the angle of the screw within the passage. This design is forgiving with respect to the exact positioning of the screw relative to the passage and to the bone until the locking thread run out at the thrust face mates with the thrust face run out of the female thread and smoothly and securely locks the screw in position relative to the plate.

OBJECTS OF THE INVENTION

It is an object of the first aspect of the invention to provide a vertebral cage that acts to fix and maintain the proper relative position of adjacent vertebrae and to hold bone graft material so as to promote fusion of these vertebrae.

A further object of this aspect of the invention is to provide a vertebral cage having a solid smooth and fluid anterior wall surface which minimizes potentially abrasive edges on the anterior face and having screw passages there through to enable the angled fixation through the respective end plates of the adjacent vertebrae. Moreover, the cage can be secured through the endwalls of adjacent vertebrae and using a triangular base of fixation by the placement of multiple screws in the vertebrae. Also, the cage has lateral fenestrations to permit radiographic inspection of the progress of fusion.

It is a further object of the invention to provide a wedge shaped vertebral cage having a high friction surface with projections inclined to resist backing out of position. Additionally, the cage has a peripheral outline design to accept and transfer loading from the cortical rings of the adjacent vertebrae.

It is an object of a second aspect of the invention to provide a self-locking base screw assembly wherein the female threads of screw receiving passage is configured to allow axial translation and limited variable angulation of the screw within the passage until the screw is tightened into a locked position.

It is thus further an object of both aspects of the invention to provide a vertebral cage having threaded angular screw passages which are anteriorly accessible and which allow a bone screw to be locked into the passage with minimal interpretation to the fluid anterior surface of the cage.

BRIEF DESCRIPTION OF THE DRAWINGS

FIG. 9 is a first side view of the fixation screw of FIG. 8;

FIG. 10 is a second side view of the fixation screw of FIG. 9 rotated 90 degrees;

FIG. 11 is a top view of the screw of FIG. 8;

FIG. 12 is a bottom view of the screw of FIG. 8;

FIG. 13 is a cross section taken along line 13—13 of FIG. 10;

FIG. 14 is an enlarged detail of the male cancellous thread of FIG. 13; and

FIG. 15 is an enlarged detail of the male locking thread of FIG. 13.

DETAILED DESCRIPTION OF THE INVENTION

Figure 1:
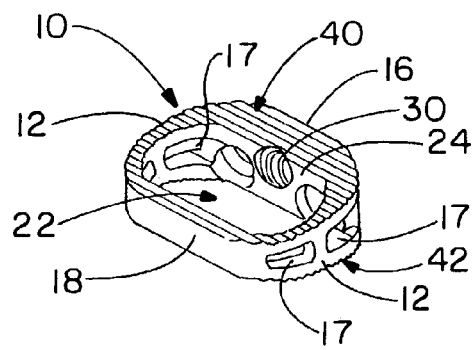
FIG. 1 is a top rear perspective view of the vertebral cage of the present invention.
Figure 2:
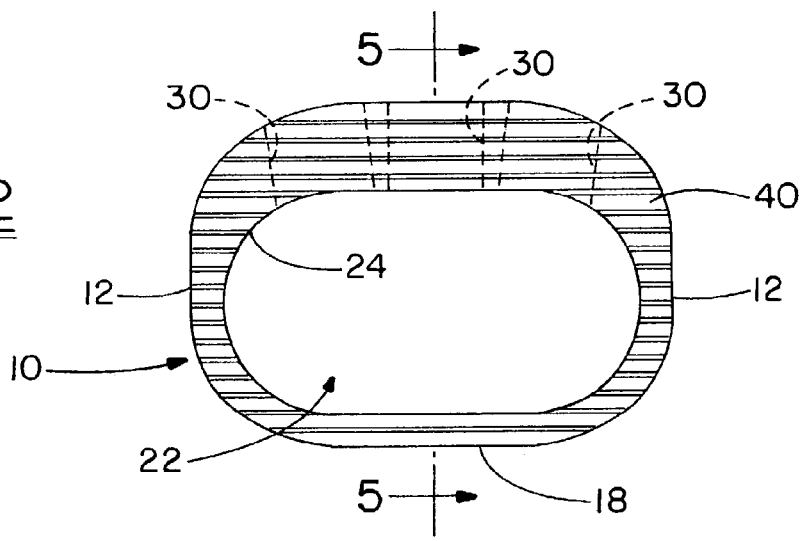
FIG. 2 is a top view of the vertebral cage of FIG. 1.

The present invention provides a vertebral space or cage, shown generally in FIG. 1. The cage 10 has a bracelet or oval peripheral shape with opposing front 16 and rear 18 walls that are generally solid, and are connected by curved side walls 12, that each include double openings, or fenestrations 17 that have a substantially rhomboid outline to maximize the area of visual access to the interior of the cage. The cage is hollow with a center opening 22 defined by a smooth continuous interior surface 24 that generally corresponds to the smooth continuous exterior surface of the cage 10. Further, the cage 10 includes a taper decreasing in height from front to back to provide a wedge shape which is lower at the back (i.e. posterior wall). Differing size cages may be provided with differing amounts of taper depending on the level of the spine where the cage is being implanted. Typically the cage is used to replace a disc, however, it is possible that the cage could be sized and used for replacement of a vertebral body and its adjacent vertebral discs. The center opening is for the inclusion of a suitable bone graft material used to promote fusion.

At the front or anterior surface 16, the cage 10 has a substantially solid wall including a plurality of angled screw passages 30. Preferably, there are three passages, with one angled downward, 34 and two 32 having a corresponding degree of angle upward. Of course, the cage can be inverted, or the screws can have one angled upward and two angled downward. A suitable range for the angle from a horizontal plane is from about 10° to about 50° and preferably from about 20° to about 30° and most preferably from about 23° to about 27°. Further the anterior wall includes a pair of parallel recesses 36 that can be used alone, or in combination with a pair of lateral recesses 38 for instrumentation for implantation. The exterior surface 26 of the anterior wall is substantially "flat" or smoothly, fluidly continuous with a contiguous, i.e. co-planar, access opening 36 to a plurality (i.e., two and preferably three) of angled and preferably internally threaded passages. These passages 30 permit fixation means, and preferably screws 60 to be inserted through the anterior wall into the end walls of the adjacent vertebrae.

Figure 7:
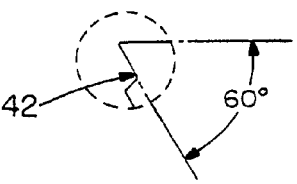
FIG. 7 is an enlarged detail showing the cross-section of the inclined projections shown in FIG. 5.
Figure 8:
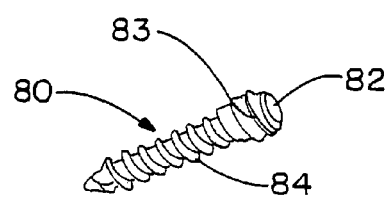
FIG. 8 is a top perspective view of the fixation screw in accordance with the invention.

The top and bottom surfaces 40, 42 of the cage 10 has a high friction surface to resist the force pushing the wedge forward out of position between the vertebrae. Preferably, this surface is a toothed, or ratchet surface that is inclined shown in FIG. 7. Of course, other contoured high friction surfaces could be used, having a combination of grooves and or peaks or roughened or machined contours to act to inhibit slippage.

A second aspect of the invention relates to the provision of a locking thread on the screw 80 and in the implant 10. This self-locking assembly comprises a specifically designed screw internally threaded through passage 34 in conjunction with a locking thread 83 on the head 82 of the fixation screw which also includes a bone thread 84. These internal or "female" threads exceed the generally acceptable tolerances for the external or "male threads of the fixation screws. The pitch is about 0.1 inch and is the same for the male and female locking threads, however, the width of the thread face is larger for the female thread 34 than the male thread 83. This width for the male locking thread 83 is larger by about 0.02 inch than for the threaded portion 34 of the cage. The depth of the thread 83 is the difference in a direction transverse to the longitudinal axis between the major diameter 95 and minor diameter of the thread 83.

The cancellous thread 84 on a first longitudinal screw area 90 has a typical asymmetrical cross-section with a sharp spiral edge 93, while the locking thread 83 on the second screw area 92 (i.e., the head) has a symmetrical trapezoidal cross sectional shape which is about 60° on the front thrust surface 94 or leading surface and the same on the back surface 96 measured from the flat transverse plane of the spiral face 98.

Essentially, the male thread 83 has a narrower foot print with a smaller major diameter (by 0.008) whereas the female thread has a narrower spiral top ramp 104 and a wider thread face 105 and bottom ramp 106 that corresponds in width to top ramp 104. This allows the screw to be translated along the longitudinal axis which will change the relative radial position of the spiral thread at the point of entry in the cage. Also, there is play with respect to the angle of the screw within the passage. This design is forgiving with respect to the exact positioning of the screw relative to the passage and to the bone until the locking thread run out 110 at the thrust face mates with the thrust face run out of the female thread and smoothly and securely locks the screw 80 in position relative to the cage 10 through the end plates into the cancellous portion of adjacent upper and lower vertebrae.

The cage and thread are made from suitable strong and bio-compatible material such as titanium, surgical grade stainless, carbon composite, ceramic, and may be made from the same or different material.

Figure 3:
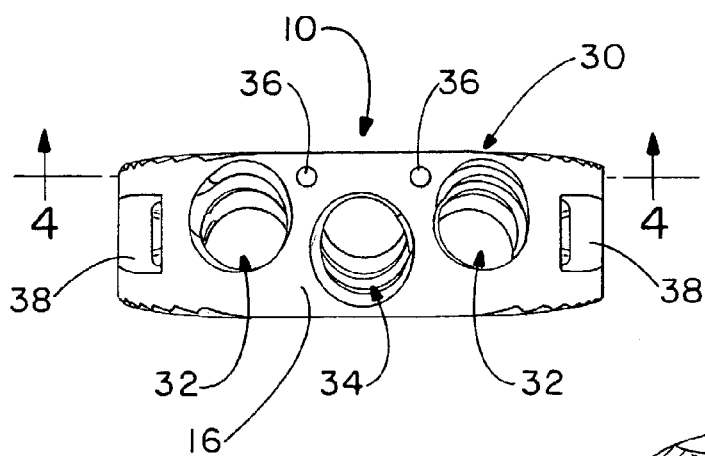
FIG. 3 is a front view of the vertebral cage of FIG. 1.
Figure 4:
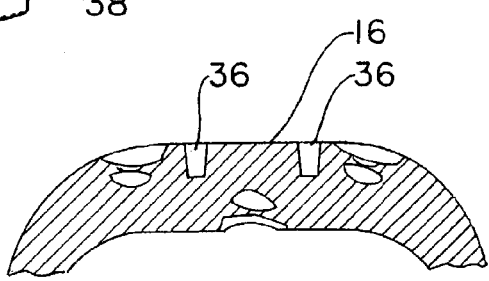
FIG. 4 is a cross-section taken along line 4—4 of FIG. 3.
Figure 5:
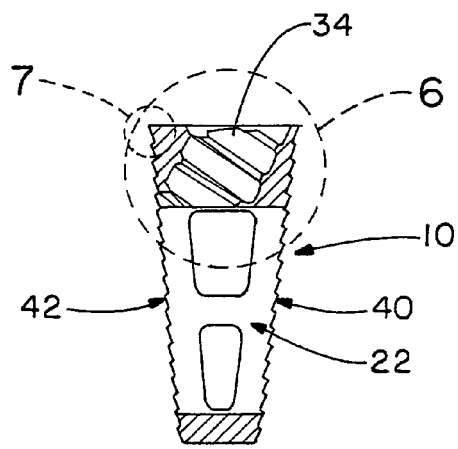
FIG. 5 is a cross-section taken along line 5—5 of FIG. 2.
Figure 6:
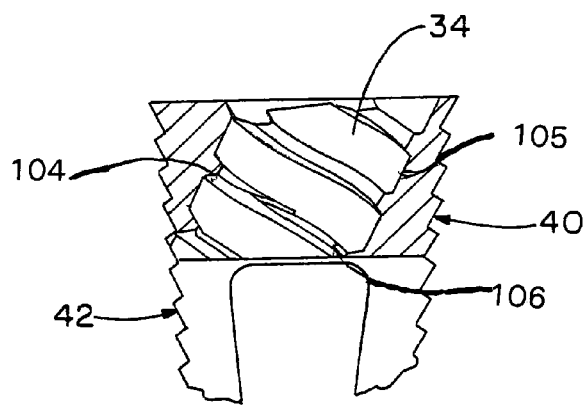
FIG. 6 is an enlarged detail of the female thread of FIG. 5.

Typically, the spinal implant surgery which utilizes the cage of the present invention begins with removal of the indicated biological material, such as a total dissectomy. The cage is subsequently filled with the selected bone graft material, and then impacted into the disc space, for example, by using a instrument that has a pair of projections that are aligned in the pair of recesses 36, and surrounding these, there is a flat area that allows the transmission of force so as to enable the cage to be tapped into place. A shadow of the area of engagement is shown in the dashed line in FIG. 3. This cooperation is another advantage enable by the smooth anterior face of the cage. Guide holes for the fixation screws are made by using a drill guide that is self-centering in the screw passages and which is cannulated for the use of a guide pin which is tapped into place to form a guide for the screws. It is important to achieve proper placement of the guide holes which causes the self-tapping screws to thread properly in these holes, and ultimately in the threaded passages. The screws are threaded in until the locking geometry engages. This is the female thread run out engaged by the male thread geometry.

While in accordance with the patent statutes the best mode and preferred embodiment have been set forth, the scope of the invention is not limited thereto, but rather by the scope of the attached claims.

What is claimed is:

1. A vertebral cage having a front wall terminating at both lateral sides in a side wall, and a rear wall terminating at both lateral sides, said side walls curving so as to join said lateral sides of said rear wall to provide a single continuous exterior surface, said cage further including a center opening and said front wall including at least three angled screw passages each passage having an internally threaded access opening defining a plane co-planar with the exterior surface wherein each of two angled passages has a longitudinal axis that intersects the center opening toward an inferior direction of the cage and one of the passages has a longitudinal axis that intersects the center opening toward a superior direction of the cage.

2. A vertebral cage as set forth in claim 1 wherein the front wall, the rear wall and the side walls together define a top edge and a bottom edge each having a high friction surface.

3. A vertebral cage as set forth in claim 2 wherein said high friction surface is a toothed surface.

4. A vertebral cage as set forth in claim 3 wherein said toothed surface is inclined toward the rear wall of the cage.

5. A vertebral cage as set forth in claim 1 wherein the front wall further includes at least one recess for the implantation of the cage.

6. A vertebral cage as set forth in claim 1 wherein said access opening has a spiral face to form a female thread recess for a fixation member, and a fixation member having external locking threads to form a mating male threads which correspond to the internal threads having a spiral face, wherein the internal threads and the external threads have the same pitch, but the major diameter of the internal threads is larger than the major diameter of the external threads and the depth of the internal threads is greater than the depth of the external threads so as to permit the axial translation of the fixation member in the passage.

7. A vertebral cage as set forth in claim 6 wherein male thread has a face having a first width and the female thread has a face having a second width and wherein the first width is substantially smaller than the second width.

8. A vertebral cage as set forth in claim 7 wherein the width of the first thread face is from about 50% to about 85% of the width of the second thread face.

9. A vertebral cage as set forth in claim 8 wherein the width of the first thread face is from about 55% to about 75% of the width of the second thread face.

10. A vertebral cage as set forth in claim 9 wherein the width of the first thread face is from about 60% to about 70% of the width of the second thread face.

11. A vertebral cage as set forth in claim 10 wherein the width of the first thread face is about ⅔ of the width of the second thread face.

12. A vertebral cage as set forth in claim 6 wherein the longitudinal distance needed to achieve one full rotation of thread spiral is the same for the male and female locking thread.

13. A vertebral cage as set forth in claim 12 wherein the depth of the male thread is from about 70% to 98% of the depth of the corresponding female thread.

14. A vertebral cage as set forth in claim 13 wherein the depth of the male thread is from about 80% to 95% of the depth of the corresponding female thread.

15. A vertebral cage as set forth in claim 14 wherein the depth of the male thread is from about 85% to 95% of the depth of the corresponding female thread.

16. A vertebral cage as set forth in claim 6 wherein the fixation member has a longitudinal screw area having a first section and a second section; the first section having a cancellous thread with an asymmetrical cross sectional shape and a sharp spiral edge, and the second section having a thread with a symmetrical trapezoidal cross sectional shape.

17. A vertebral cage as set forth in claim 16 wherein the second section has a trapezoidal cross sectional shape having a front thrust surface with an angle of from about 40° to about 80°.

18. A vertebral cage as set forth in claim 17 wherein the second section has a trapezoidal cross sectional shape having a front thrust surface with an angle of from about 50° to about 70°.

19. A vertebral cage as set forth in claim 18 wherein the second section has a trapezoidal cross sectional shape having a front thrust surface with an angle of from about 55° to about 65°.

20. A vertebral cage as set forth in claim 19 wherein the width of the spiral face is less than 0.04 inches deep.

21. A vertebral cage having a front wall terminating at both lateral sides in a side wall, and a rear wall terminating at both lateral sides, said side walls curving so as to join said lateral sides of said rear wall to provide a single continuous exterior surface, the continuous exterior surface including a center opening and having a top edge which defines a top plane and a bottom edge which defines a bottom plane, front wall of the cage including not more than three angled screw openings capable of receiving screws, where a first screw opening has a longitudinal axis angled through one of the top plane or the bottom plane and each of the second two screw openings has a longitudinal axis angled through the other of the top plane or the bottom plane, and the first opening is located between the second two openings and wherein each of the screw openings has an internally threaded recess having a spiral face to form a female thread recess for a thread of one of the screws, and a screw having a head with external threads to form a mating male thread which correspond to the internal threads of the screw openings and having a spiral face, wherein the internal threads and the external thread have the same pitch, but the major diameter of the internal threads is larger than the major diameter of the external threads and the depth of the spiral face of the internal thread is greater than the depth of the spiral face of the external thread so as to permit the axial translation of the fixation member in the passage.

22. A vertebral cage as set forth in claim 21 wherein screw openings extend completely through the front wall of the cage and the exterior surface of the front wall is substantially fluid about the screw openings.

23. A vertebral cage as set forth in claim 22 wherein the threads of the screw openings are complete throughout the length of the screw openings.

24. A vertebral cage having a front wall terminating at both lateral sides in a side wall, and a rear wall terminating at both lateral sides, said side walls curving so as to join said lateral sides of said rear wall to provide a single continuous, exterior surface, the continuous exterior surface including a center opening and having a top edge which defines a top plane and a bottom edge which defines a bottom plane, front wall of the cage including at least three angled internally threaded screw openings capable of receiving screws having externally threaded heads which mate with the threads of the screw openings, where a first screw opening has a longitudinal axis angled through one of the top plane or the bottom plane and each of the second two screw openings has a longitudinal axis angled through the other of the top plane or the bottom plane, and wherein the screw openings each have an internally threaded recess having a spiral face to form a female thread recess for a thread of one of the screws, and a screw having a head with external threads to form a mating male thread which correspond to the internal threads of the screw opening and having a spiral face, wherein the internal threads and the external threads have the same pitch, but the major diameter of the internal threads is larger than the major diameter of the external threads and the depth of the spiral face of the internal threads is greater than the depth of the spiral face of the external threads so as to permit the axial translation of the fixation member in the passage.

25. A vertebral cage as set forth in claim 24 wherein the front wall, the rear wall and the side walls together define a top edge and a bottom edge each having a high friction surface.

26. A vertebral cage as set forth in claim 25 wherein said high friction surface is a toothed surface.

27. A vertebral cage as set forth in claim 26 wherein said toothed surface is inclined toward the rear wall of the cage.

28. A vertebral cage as set forth in claim 27 wherein the front wall further includes at least one recess for the implantation of the cage.

29. A vertebral cage having a front wall terminating at both lateral sides in a side wall, and a rear wall terminating at both lateral sides, said side walls curving so as to join said lateral sides of said rear wall to provide a single continuous exterior surface, said cage further including a center opening and said front wall including an interior surface defining the center opening and an opposing exterior surface and three angled threaded screw passages to provide a triangular base of fixation, each screw passage extending from the interior surface of the front wall to the exterior surface of the front wall and including a thread run out at the exterior surface of the front wall wherein each of two inferior passages has a longitudinal axis that intersects the center opening toward an inferior direction of the cage and one of the passages has a longitudinal axis that intersects the center opening toward a superior direction of the cage.

30. A vertebral cage as set forth in claim 29 wherein the front wall, the rear wall and the side walls together define a top edge and a bottom edge each having a high friction surface.

31. A vertebral cage as set forth in claim 30 wherein said high friction surface is a toothed surface.

32. A vertebral cage as set forth in claim 31 wherein said toothed surface is inclined toward the rear wall of the cage.

33. A vertebral cage as set forth in claim 32 wherein the front wall further includes at least one recess for the implantation of the cage.

34. A vertebral cage as set forth in claim 29 wherein the front wall includes only three angled passages.

35. A vertebral cage as set forth in claim 29 having an internally threaded recess to form a female thread for a fixation member and a fixation member having external locking threads to form a mating male thread which corresponds to the internal threads; wherein the external locking threads have a first profile which is smaller than the corresponding second profile of the female locking thread.

36. A vertebral cage as set forth in claim 35 wherein the width of the male thread profile is from about 50% to about 85% of the corresponding thread profile of the female thread.

37. A vertebral cage as set forth in claim 36 wherein the width of the male thread profile is from about 60% to about 70% of the corresponding thread profile of the female thread.

* * * * *